(12) United States Patent
Zuo et al.

(10) Patent No.: US 10,309,885 B2
(45) Date of Patent: Jun. 4, 2019

(54) METHOD AND APPARATUS FOR WATER-BASED MUD FILTRATE CONTAMINATION MONITORING IN REAL TIME DOWNHOLE WATER SAMPLING

(71) Applicant: Schlumberger Technology Corporation, Sugar Land, TX (US)

(72) Inventors: Youxiang Zuo, Sugar Land, TX (US); Adriaan Gisolf, Houston, TX (US); Julian Pop, Houston, TX (US); Oliver Mullins, Houston, TX (US); Chetankumar Desai, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 1179 days.

(21) Appl. No.: 14/085,550

(22) Filed: Nov. 20, 2013

(65) Prior Publication Data

US 2015/0135814 A1    May 21, 2015

(51) Int. Cl.
| | | |
|---|---|---|
| *G01N 9/00* | (2006.01) | |
| *E21B 49/08* | (2006.01) | |
| *G01N 9/36* | (2006.01) | |
| *G01N 33/28* | (2006.01) | |

(52) U.S. Cl.
CPC .............. *G01N 9/00* (2013.01); *E21B 49/08* (2013.01); *G01N 9/36* (2013.01); *G01N 33/2823* (2013.01)

(58) Field of Classification Search
CPC .. G01N 9/00; G01N 9/04; G01N 9/26; G01N 9/36; E21B 49/08; E21B 49/081–49/082; E21B 49/084; E21B 49/086–49/088; E21B 49/10; E21B 2049/085
See application file for complete search history.

(56) References Cited

U.S. PATENT DOCUMENTS

| | | |
|---|---|---|
| 6,729,400 B2 | 5/2004 | Mullins et al. |
| 7,028,773 B2 | 4/2006 | Fujisawa et al. |
| 2003/0145988 A1 | 8/2003 | Mullins et al. |

(Continued)

FOREIGN PATENT DOCUMENTS

WO    2012094007 A2    7/2012

OTHER PUBLICATIONS

Al-Musharfi et al., The Challenge of Water Sampling with a Wireline Formation Tester in a Transition Zone, May 25-28, 2008, SPWLA 49th Annual Logging Symposium, pp. 1-14.*

(Continued)

*Primary Examiner* — Toan Le
(74) *Attorney, Agent, or Firm* — Michael Dae (57) ABSTRACT

A method for contamination monitoring includes measuring water based mud filtrate density and resistivity at downhole conditions, logging properties of a downhole fluid to find at least a resistivity and a density of a fluid sample at the downhole conditions, establishing a linear relationship between a water based mud filtrate conductivity at downhole conditions and the water based mud filtrate density at the downhole conditions, determining a density and a resistivity for native formation water, estimating a density for water based mud filtrate using the linear relationship between conductivity and density, and estimating a water based mud filtrate contamination.

12 Claims, 5 Drawing Sheets

(56) References Cited

U.S. PATENT DOCUMENTS

| | | |
|---|---|---|
| 2004/0000400 A1 | 1/2004 | Fujisawa et al. |
| 2005/0182566 A1 | 8/2005 | DiFoggio |
| 2007/0238180 A1 | 10/2007 | DiFoggio et al. |
| 2014/0180591 A1 | 6/2014 | Hsu et al. |

OTHER PUBLICATIONS

Villareal, et al., "Characterization of Sampling-While-Drilling Operations", SPE 128249, IADC/SPE Drilling Conference and Exhibition, New Orleans, Louisiana, USA, Feb. 2-4, 2010.

Zuo, et al., "A New Method for OBM Decontamination in Downhole Fluid Analysis", IPTC 16524—6th International Petroleum Technology Conference, Beijing, China, Mar. 26-28, 2013.

McCain, "The Properties of Petroleum Fluids, 2nd Edition", PennWell Publishing, 1990, pp. 444-450.

International Search Report and Written Opinion issued in PCT/US2014/066434 on Feb. 24, 2015, 11 pages.

\* cited by examiner

METHOD AND APPARATUS FOR WATER-BASED MUD FILTRATE CONTAMINATION MONITORING IN REAL TIME DOWNHOLE WATER SAMPLING

CROSS-REFERENCE TO RELATED APPLICATIONS

None.

FIELD OF THE INVENTION

Aspects of the disclosure relate to contamination monitoring. More specifically, aspects of the disclosure relate to method and apparatus for water-based mud filtrate contamination monitoring in real time downhole water sampling.

BACKGROUND INFORMATION

Water based drilling mud filtrate contamination monitoring is a large challenge in downhole formation water sampling. Currently, there are no conventional downhole real time methods available for quantitative water based drilling mud filtrate contamination monitoring during water sampling with the lone exception of using special dyes mixed with the water based drilling mud.

Use of special dyes adds complexity to drilling operations. Dyes added should be compatible with the drilling mud and the formation and fluids for the formation that are expected to be extracted. Some dyes can be expensive and additional work is required for injection of the dye into the fluid stream.

Special dyes are expensive for operators in other ways as operators need time to add the dye to wellbore mud systems as rig time can be very constrained. These special dyes, because of the complexities described above, are carefully crafted such that they provide minimal harm from a technological and cost perspective.

SUMMARY

The following summary is but an example description of one embodiment described. The disclosure in the summary should not be considered limiting. A method for contamination monitoring is described entailing measuring a water based mud filtrate density and a water based mud filtrate resistivity at surface conditions, converting the measured water based mud filtrate density and resistivity to downhole conditions, logging properties of a downhole fluid to find at least a resistivity and a density of a fluid sample at the downhole conditions, establishing a linear relationship between a water based mud filtrate conductivity at downhole conditions and the water based mud density at the downhole conditions, determining an existence of a high quality pressure gradient at the downhole conditions, fitting at least one of a density and a resistivity data using a power function and obtaining at least one of a density and a resistivity for native formation water when no high quality pressure gradient exists, estimating a density from the pressure from the high quality gradient when the high quality pressure gradient exists; estimating a resistivity for native formation water, using the linear relationship between the conductivity and the density, estimating a density for water based mud filtrate using the linear relationship between conductivity and density and estimating a water based mud filtrate contamination.

DETAILED DESCRIPTION

Aspects described relate to a method and apparatus for water-based mud filtrate contamination monitoring in real time downhole water sampling. The method and system provided are used in downhole apparatus in the exploration of oil and gas in geological formations. Such techniques greatly enhance the capability of engineers and operators to economically find hydrocarbons beneath the ground surface.

For the purposes of this detailed description, it is assumed that the fluid in the downhole flowline consist of two components: water based mud filtrate and native formation water. The following mixing rule can be used for resistivity:

$$\frac{1}{R^n} = \frac{\eta}{R_{whm}^n} + \frac{1-\eta}{R_{fw}^n} \qquad \text{Equation 1}$$

where R, $\eta$, $R_{whm}$ and $R_{fw}$ are the resistivity of the mixture (water based mud filtrate and formation water—formation water contaminated by water based mud filtrate), water based mud filtrate contamination fraction, resistivity of the pure water based mud filtrate and resistivity of the native formation water. The value n is an exponent (default n=1), which may be used as an adjustable parameter.

Rearranging Equation 1 above, the result obtained is the water based mud filtrate contamination based on resistivity measured by downhole fluid analysis:

$$\eta = \frac{\frac{1}{R^n} - \frac{1}{R_{fw}^n}}{\frac{1}{R_{whm}^n} - \frac{1}{R_{fw}^n}} = \frac{R_{whm}^n}{R^n} \frac{R^n - R_{fw}^n}{R_{whm}^n - R_{fw}^n} \qquad \text{Equation 2}$$

where R is measured by downhole fluid analysis during water sampling, which is a function of time (or pumpout volume). In Equation 2, two endpoints—resistivity of pure water based mud filtrate ($R_{whm}$) and native formation water ($R_{fw}$) should be known to obtain $\eta$. It should be noted that resistivity contrast between the pure water based mud filtrate and native formation water should be sufficient in order to use Equation 2.

Below is a description of using density for water based mud filtrate contamination monitoring. The contaminated fluid is divided into two components, the pure water based mud filtrate and the native formation water. It is assumed that the mixing of the water based mud filtrate and native formation water is ideal, i.e. producing no excess volume during mixing:

$$V^{mol} = x_{wbm} V_{wbm}^{mol} + (1 - x_{wbm}) V_{fw}^{mol} \qquad \text{Equation 3}$$

where $V^{mol}$ and x are the molar volume and mole fraction. Subscripts wbm and fw represent the pure water based mud filtrate and native formation water. The molar volume and mole fraction can be changed into density (ρ) and water based mud filtrate contamination volume fraction (η) at downhole conditions by:

$$\rho = \eta \rho_{wbm} + (1-\eta)\rho_{fw} \quad \text{Equation 4}$$

Rearranging Equation 4, the water based mud filtrate contamination volume fraction is expressed as:

$$\eta = \frac{\rho_{fw} - \rho}{\rho_{fw} - \rho_{wbm}} \quad \text{Equation 5}$$

The value η can be related to the weight fraction of water based mud filtrate contamination at downhole conditions by:

$$w_{wbm} = \frac{\eta \rho_{wbm}}{\rho} = \frac{\rho_{wbm}(\rho_{fw} - \rho)}{\rho(\rho_{fw} - \rho_{wbm})} \quad \text{Equation 6}$$

In Equations 5 and 6, two endpoints—densities of pure water based mud filtrate ($\rho_{wbm}$) and native formation water ($\rho_{fw}$) should be known to obtain η. Density contrast between the pure water based mud filtrate and native formation water are sufficient in order to use Equations 5 and 6 for water based mud filtrate contamination monitoring. Equalizing Equations 2 and 5:

$$\eta = \frac{\frac{1}{R^n} - \frac{1}{R_{fw}^n}}{\frac{1}{R_{wbm}^n} - \frac{1}{R_{fw}^n}} = \frac{\rho_{fw} - \rho}{\rho_{fw} - \rho_{wbm}} \quad \text{Equation 7}$$

Figure 1:
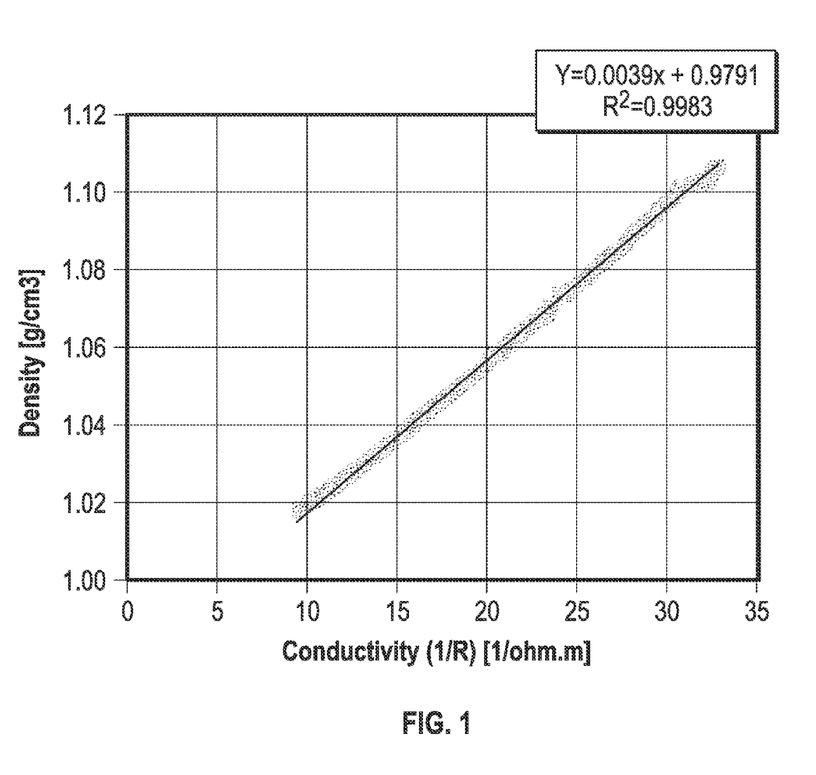
FIG. 1 is a graph of density versus conductivity for water sampling with water based mud in real time.

For specified water based mud filtrate and formation water, the resistivity ($R_{wbm}$ and $R_{fw}$) and density ($\rho_{wbm}$ and $\rho_{fw}$) of the pure water based mud filtrate and native formation water are fixed. Therefore, density (ρ) and reciprocal of resistivity (conductivity, 1/R) is linear (assuming n=1). FIG. 1 shows the real time results of density versus conductivity. It should be noted that this linear relation is very useful for determining endpoints for native formation water and/or pure water based mud filtrate. This also constrains exponent in the power function fitting model as provided below.

The two endpoints for pure water based mud filtrate and native formation water are determined. A determination of resistivity and density of pure water based mud filtrate ($R_{wbm}$ and $\rho_{wbm}$) occurs. To obtain the endpoints for pure water based mud filtrate entails measuring the resistivity and density of the pure water based mud filtrate on the surface if pure water based mud filtrate is available before logging at different temperatures and pressure covering the entire set of reservoir conditions. Next, the measured resistivity and density of the pure water based mud filtrate are correlated with the following functions of temperature and pressure:

$$R_{wbm} = \Sigma_{i=0}^{2} \Sigma_{j=0}^{1} a_{ij} P^i T^j \quad \text{Equation 8}$$

$$\rho_{wbm} = \Sigma_{i=0}^{2} \Sigma_{j=0}^{1} b_{ij} P^i T^j \quad \text{Equation 9}$$

where $a_{ij}$'s and $b_{ij}$'s are coefficients of the polynomial functions, which are regressed by matching the measured resistivity and density data on the surface for different types of water based mud filtrates.

In another embodiment, the resistivity of pure water based mud filtrate is measured at surface conditions and converted to flowline conditions. The density of pure water based mud filtrates is measured at surface conditions and converted to flowline conditions.

Next, the linear relationship between reciprocal of resistivity (conductivity) and density can be used to estimate either density or resistivity of the pure water based mud filtrate if resistivity or density of the pure water based mud filtrate is known. Downhole cleanup data may be used.

At the beginning of cleanup, 100% water based mud filtrate may be pumped in a flowline. The downhole fluid analysis measured resistivity and density at the beginning of cleanup may be considered as the resistivity and density of the pure water based mud filtrate. In particular, when multiple downhole fluid analysis stations are available or when the filtrate invasion is very deep, a reasonable value may be measured or estimated.

Resistivity and density of native formation water ($R_{fw}$ and $\rho_{wf}$) may be determined. The density of native formation water can be determined as follows:
a) Pretest pressure (pressure gradient) data can be used to determine density of the native formation water-density endpoint for the native formation water, or
b) During cleanup, live formation water density can also be fitted by the following power function:

$$\rho = \rho_{wf} - \beta V^{-\gamma} \quad \text{Equation 10}$$

where ρ and V are the density and pumpout volume (can be replaced by time t) measured by downhole fluid analysis; $\rho_{wf}$, β and γ are three adjustable parameters. Once good density data regression is obtained, density ($\rho_{wf}$) for the native formation water can be extrapolated when the pumpout volume (time) approaches infinity. For focus sampling, V can be replaced by the volume in the sample line (and/or guard line) or by the total volume (summation of sample and guard line volumes). In this case, p is replaced by (subscripts s and g stand for sample and guard, Q is the flowrate):

$$\rho = \frac{\rho_s Q_s + \rho_g Q_g}{Q_s + Q_g} \quad \text{Equation 11}$$

The resistivity of native formation water can be determined as follows:
a) The resistivity of native formation water can be determined by the linear relationship between reciprocal of resistivity (conductivity) and density once density is determined by the method mentioned previously.
b) The resistivity of native formation water may be estimated from Archies expression by assuming a clean sandstone formation for which m and n have the value of 2 and $S_w$=1.

$$R_{wf} = \frac{1}{a} \varphi^m S_w^n R_t \approx \frac{1}{.81} \varphi^2 R_t \quad \text{Equation 12}$$

where φ is the formation porosity and $R_t$ is the formation resistivity, which can be measured by conventional wireline logs.
c) The resistivity of native formation water can be determined by the fitting model as done for density:

$$\frac{1}{R} = \frac{1}{R_{wf}} - \beta V^{-\gamma} \qquad \text{Equation 13}$$

where R and V are the resistivity and pumpout volume (can be replaced by time t) measured by downhole fluid analysis; $R_{wf}$, $\beta$ and $\gamma$ are three adjustable parameters. Once resistivity data regression is obtained, resistivity ($R_{wf}$) for the native formation water can be extrapolated when the pumpout volume (time) approaches infinity. For the focus sampling, V can be replaced by the volume in the sample line (and/or guard line) besides total volume (summation of sample and guard line volumes). In this case R is replaced by (subscripts s and g stand for sample and guard, Q is the flow rate):

$$\frac{1}{R} = \frac{\frac{1}{R_s}Q_s + \frac{1}{R_g}Q_g}{Q_s + Q_g} \qquad \text{Equation 14}$$

It should be noted that the linear relationship between reciprocal of resistivity (conductivity) and density constrains the exponent ($\gamma$) in the equations above. This means that $\gamma$ is the same value.

Additionally, the resistivity of native formation water may be directly fitted by:

$$R = R_{wf} - \beta V^{-\gamma} \qquad \text{Equation 13}$$

Once the two endpoints of resistivity and/or density are obtained, Equations 2 and 5 can be used to estimate water based mud filtrate contamination in water samples. The time required for sampling to reach a certain water based mud filtrate contamination level can be calculated by:

$$\Delta t = \frac{\Delta V}{Q_{pump}} \qquad \text{Equation 14}$$

where $\Delta t$, $\Delta V$ and $Q_{pump}$ are the time required to reach a specified water based mud filtrate contamination level, the pumpout volume required to reach the specified water based mud filtrate contamination level, and the pumpout volume flowrate (assuming to be constant).

Figure 2:
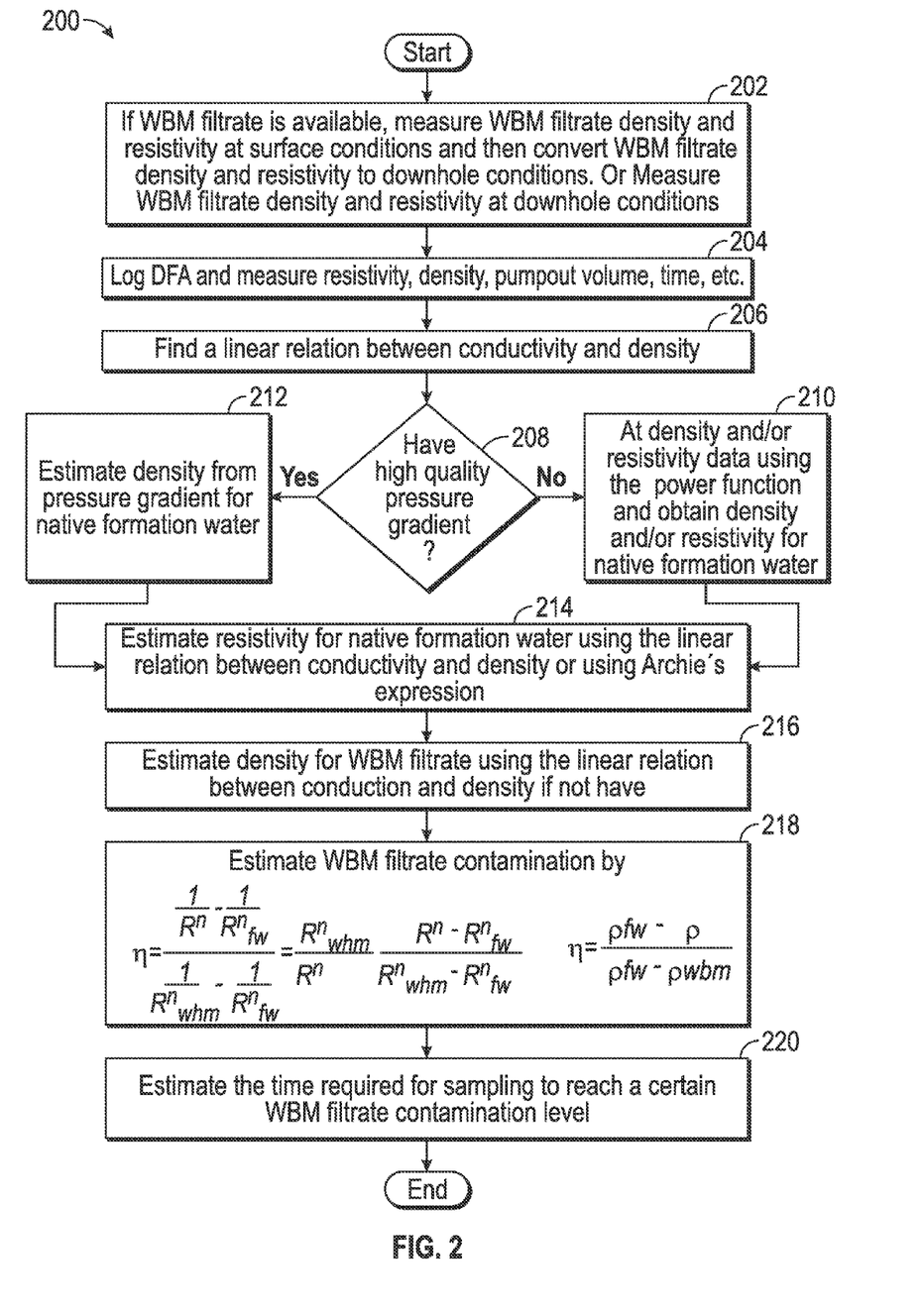
FIG. 2 is a flowchart for a method of water based mud filtrate contamination modeling.

Referring to FIG. 2, an example method 200 of performing the analysis presented above is provided. In 202, if water based mud filtrate is available, the water based mud filtrate density and resistivity are measured as surface conditions and then converted to downhole conditions. In another embodiment, the water based mud filtrate density and resistivity conditions are measured downhole. In 204, downhole fluid analysis is logged and resistivity, density, pumpout volume and time are logged. In 206, a linear relationship is found between conductivity and density. In 208, a decision is made whether there is a high quality pressure gradient. If there is no high pressure gradient, the method moves to 210 where the density is fit and/or resistivity data using the power function and the density is obtained and/or resistivity for native formation water. The method then progresses to 214. If the high pressure quality pressure gradient is available in 208, then in 212 density is estimated from the pressure gradient for native formation water. The method then progresses to 214. In 214, resistivity is estimated for native formation water using the linear relation between conductivity and density or using Archie's expression. In 216, density is estimated for water based mud filtrate using the linear relation between conduction and density. In 218, water based mud filtrate contamination is estimated. In 220, the time required for sampling to reach a certain water based mud filtrate contamination level is estimated.

Figure 3:
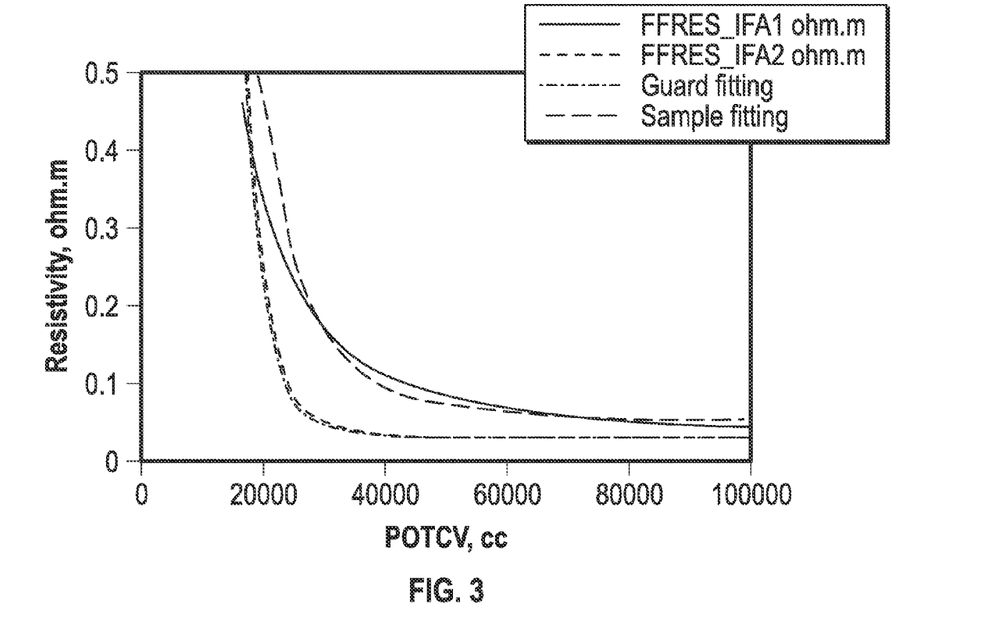
FIG. 3 is graph of resistivity variation measurement over pumpout volume obtained.

Referring to FIG. 3, the density and resistivity of the pure mud filtrate are obtained from downhole measurements at the beginning of clean up due to deep invasion. The endpoints of the native formation water are determined as follows. Resistivity variation with pumpout volume is shown in FIG. 3. The power function fitting curves are illustrated in FIG. 3. The fitting is done for the sample and guard lines respectively. Therefore, the resistivity of the native formation water is obtained from the fitting curves.

Figure 4:
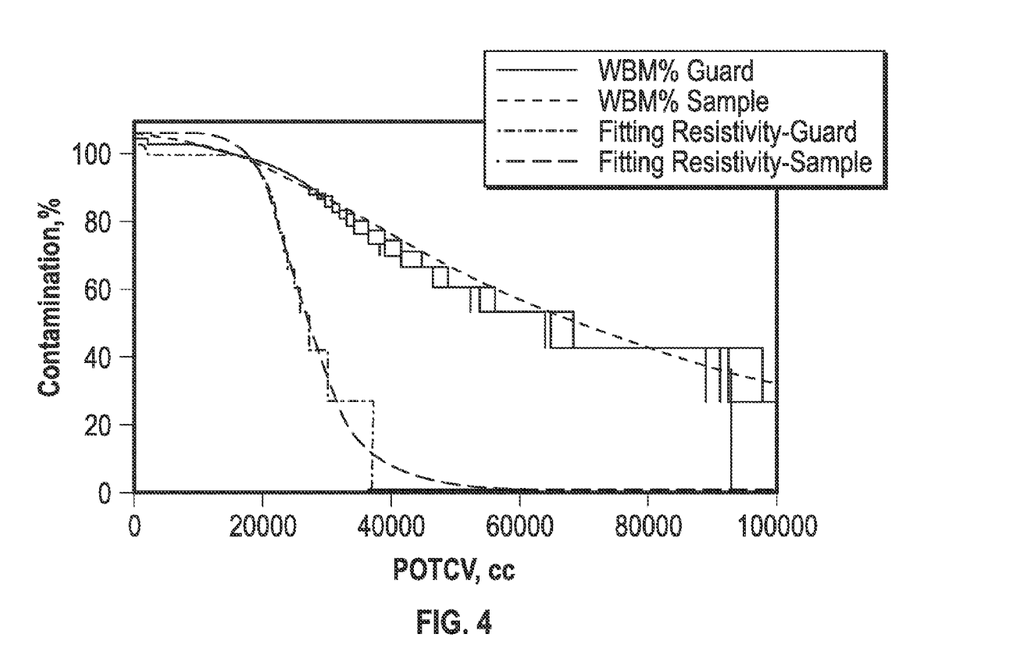
FIG. 4 is a graph of water based filtrate contamination monitoring versus pumpout volume obtained.

Referring to FIG. 4, water based mud filtrate contamination is estimated where contamination percentage is on the Y axis and volume is provided on the X axis.

Figure 5:
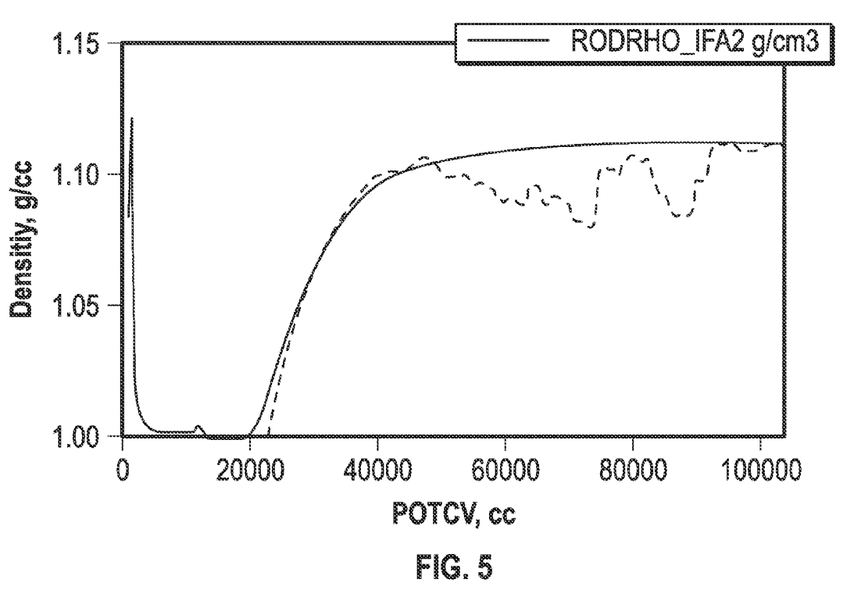
FIG. 5 is a graph of density in the sample line versus pumpout volume obtained.

Referring to FIG. 5, density fitting in the sample line is shown. Density in the guard line is not measured. The density of the native formation water is obtained from the fitting curve. Density is provided on the Y axis and volume is described in the X axis.

Figure 6:
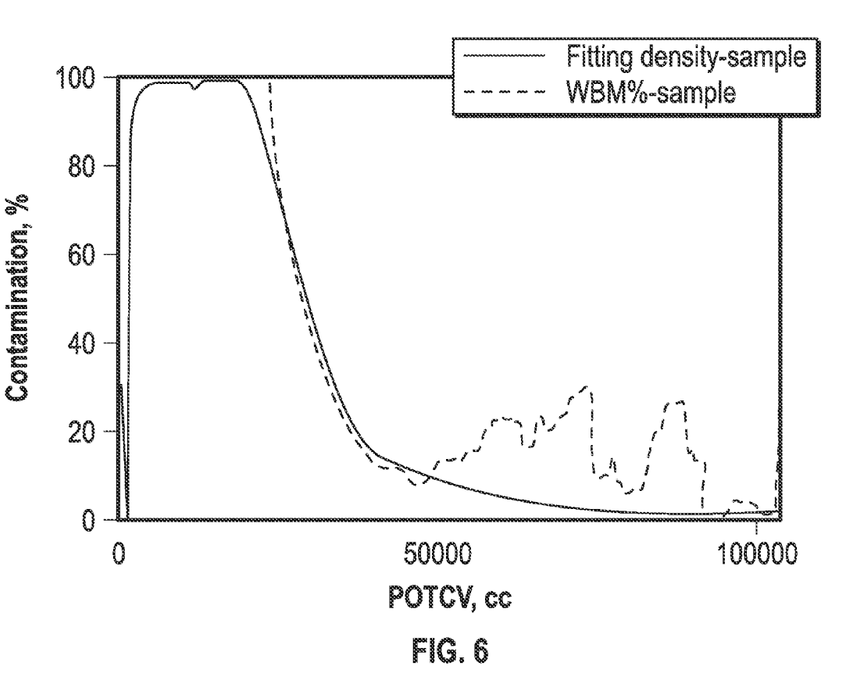
FIG. 6 is a graph of contamination percentage water based contamination versus pumpout volume obtained.

The estimated water based mud filtrate contamination in the sample line based on the density mixing rule is provided in FIG. 6. The contamination percentage in the Y axis is compared to the volume in the X axis.

Figure 7:
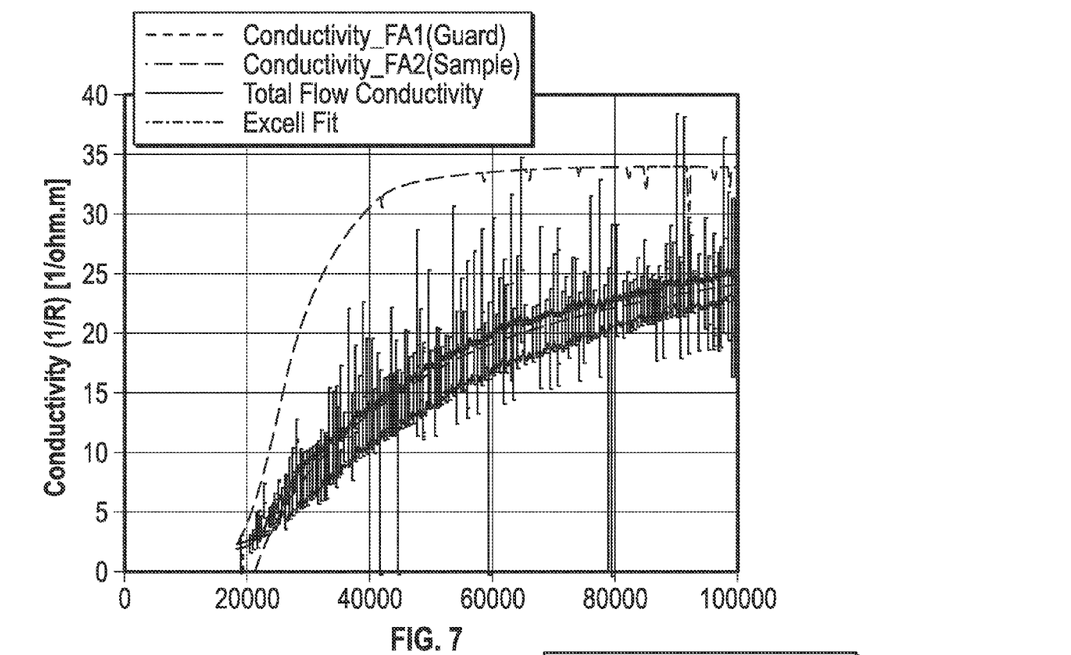
FIG. 7 is a graph of conductivity versus pumped volume.

The resistivity of the native formation water can be determined from total conductivity fitting. Referring to FIG. 7, the power function fitting for the total conductivity of the combined sample and guard lines is shown. The density and conductivity cross plot is given in FIG. 1. Once either the density or conductivity of the native formation water, the cross plot can be used to obtain either conductivity or density of the native formation water. The Y axis of the plot provides conductivity and the X axis of the plot refers to pumped volume.

Figure 8:
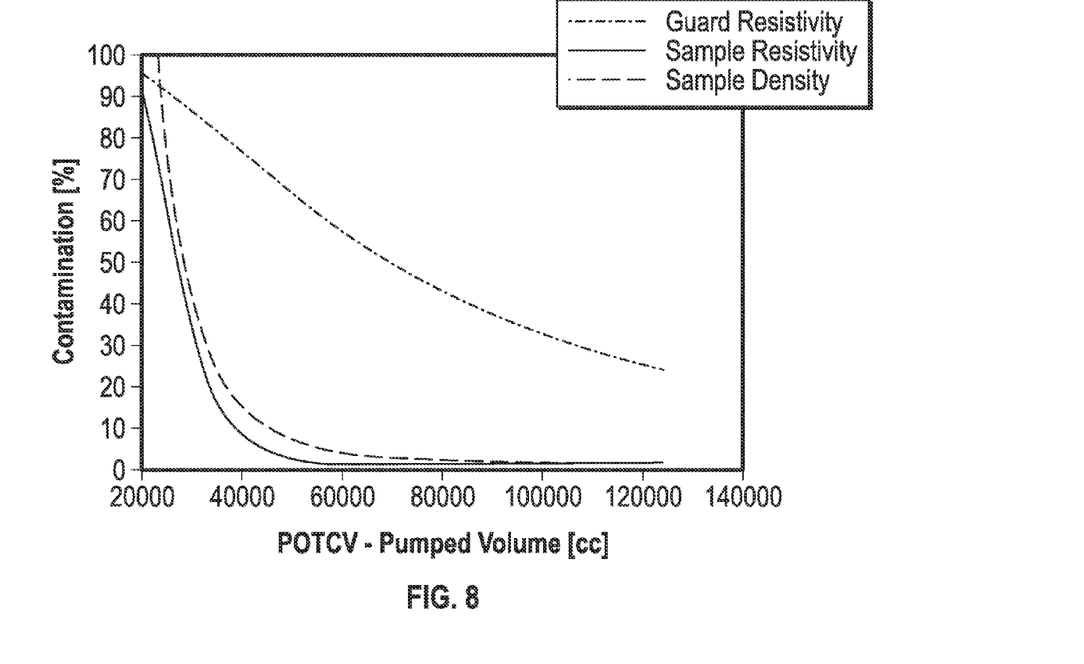
FIG. 8 is a graph of contamination percentage versus pumped volume.

Referring to FIG. 8, a comparison of the water based mud filtrate contamination estimated by the above described method is performed in the sample and guard lines. The curves stand for the water based mud filtrate contamination estimated by the resistivity and density mixing rules provided above. As can be seen, the sample line cleans up faster than the guard line.

In one example embodiment, a method for contamination monitoring is provided comprising measuring a water based mud filtrate density and a water based mud filtrate resistivity at surface conditions, converting the measured water based mud filtrate density and resistivity to downhole conditions; logging properties of a downhole fluid to find at least a resistivity and a density of a fluid sample at the downhole conditions, establishing a linear relationship between a water based mud filtrate conductivity at downhole conditions and the water based mud density at the downhole conditions, determining an existence of a high quality pressure gradient at the downhole conditions, fitting at least one of a density and a resistivity data using a power function and obtaining at least one of a density and a resistivity for native formation water when no high quality pressure gradient exists, estimating a density from the pressure from the high quality gradient when the high quality pressure gradient exists, estimating a resistivity for native formation water, using the linear relationship between the conductivity and the density, estimating a density for water based mud filtrate using the linear relationship between conductivity and density and estimating a water based mud filtrate contamination.

The method may also be accomplished wherein the estimating the resistivity for native formation water is performed using the linear relationship between the conductivity and the density.

The method may also be accomplished wherein the estimating the resistivity for native formation water is performed using Archie's expression.

The method may also be accomplished wherein the method further comprises estimating a time required for sampling to reach a water based mud filtrate contamination level.

The method may also be accomplished wherein the estimating the water based mud filtrate contamination is performed through an equation:

$$\eta = \frac{\frac{1}{R^n} - \frac{1}{R_{fw}^n}}{\frac{1}{R_{wbm}^n} - \frac{1}{R_{fw}^n}} = \frac{\rho_{fw} - \rho}{\rho_{fw} - \rho_{wbm}}.$$

The method may also be accomplished, wherein the determining the existence of the high quality pressure gradient at the downhole conditions is performed through downhole pretests.

In another example embodiment, a method for contamination monitoring is provided, comprising measuring water based mud filtrate density and resistivity at downhole conditions; logging properties of a downhole fluid to find at least a resistivity and a density of a fluid sample at the downhole conditions, establishing a linear relationship between a water based mud filtrate conductivity at downhole conditions and the water based mud density at the downhole conditions, determining an existence of a high quality pressure gradient at the downhole conditions, fitting at least one of a density and a resistivity data using a power function and obtaining at least one of a density and a resistivity for native formation water when no high quality pressure gradient exists, estimating a density from the pressure from the high quality gradient when the high quality pressure gradient exists, estimating a resistivity for native formation water, using the linear relationship between the conductivity and the density, estimating a density for water based mud filtrate using the linear relationship between conductivity and density, and estimating a water based mud filtrate contamination.

In another example embodiment, the method is accomplished wherein the estimating the resistivity for native formation water is performed using the linear relationship between the conductivity and the density.

In another example embodiment, the method is accomplished wherein the estimating the resistivity for native formation water is performed using Archie's expression.

In another example embodiment, the method described above may further comprise estimating a time required for sampling to reach a water based mud filtrate contamination level.

In another example embodiment, the method described above may be accomplished wherein the estimating the water based mud filtrate contamination is performed through an equation:

$$\eta = \frac{\frac{1}{R^n} - \frac{1}{R_{fw}^n}}{\frac{1}{R_{wbm}^n} - \frac{1}{R_{fw}^n}} = \frac{\rho_{fw} - \rho}{\rho_{fw} - \rho_{wbm}}.$$

In another example embodiment, the method described above may be accomplished wherein the determining the existence of the high quality pressure gradient at the downhole conditions is performed through downhole pretests.

While the aspects have been described with respect to a limited number of embodiments, those skilled in the art, having benefit of the disclosure, will appreciate that other embodiments can be devised which do not depart from the scope of the disclosure herein.

What is claimed is:

1. A method for contamination monitoring, comprising:
measuring a water based mud filtrate density and a water based mud filtrate resistivity at surface conditions;
converting via a downhole apparatus the measured water based mud filtrate density and resistivity to downhole conditions;
logging via the downhole apparatus properties of a downhole fluid to find at least a resistivity and a density of a fluid sample at the downhole conditions;
establishing via the downhole apparatus a linear relationship between a water based mud filtrate conductivity at downhole conditions and the water based mud filtrate density at the downhole conditions;
determining via the downhole apparatus an existence of a high quality pressure gradient at the downhole conditions;
fitting via the downhole apparatus at least one of a density and a resistivity data for native formation water using a power function and obtaining at least one of a density and a resistivity for native formation water when no high quality pressure gradient exists;
estimating via the downhole apparatus the density for native formation water from the pressure from the high quality gradient when the high quality pressure gradient exists;
estimating via the downhole apparatus the resistivity for native formation water, using the linear relationship between the water based mud filtrate conductivity and the water based mud filtrate density;
estimating via the downhole apparatus a density for water based mud filtrate using the linear relationship between the water based mud filtrate conductivity and the water based mud filtrate density; and
estimating via the downhole apparatus a water based mud filtrate contamination based on the water based mud filtrate density.

2. The method according to claim 1, wherein the estimating the resistivity for native formation water is performed using the linear relationship between the water based mud filtrate conductivity and the water based mud filtrate density.

3. The method according to claim 1, wherein the estimating the resistivity for native formation water is performed using Archie's expression $$R_{wf} = \frac{1}{a}\varphi^m S_w^n R_t \approx \frac{1}{.8}1\varphi^2 R_t$$

where
$R_{wf}$ represents resistivity of native formation water;
a represents a constant;
$\varphi$ represents a formation porosity;
m represents a cementation factor;
$S_w$ represents water saturation;
n represents a saturation exponent;
$R_t$ represents a formation resistivity.

4. The method according to claim 1, further comprising: estimating a time required for sampling to reach a water based mud filtrate contamination level.

5. The method according to claim 1, wherein the estimating the water based mud filtrate contamination is performed through an equation:

$$\eta = \frac{\frac{1}{R^n} - \frac{1}{R_{fw}^n}}{\frac{1}{R_{wbm}^n} - \frac{1}{R_{fw}^n}} = \frac{\rho_{fw} - \rho}{\rho_{fw} - \rho_{wbm}}$$

where $\eta$ represents the water based mud filtrate contamination;
R represents the resistivity of the fluid sample;
$R_{fw}$ represents the resistivity of native formation water;
$R_{wbm}$ represents the water based mud filtrate resistivity;
n represents an adjustable parameter;
$\rho_{fw}$ represents the density of native formation water;
$\rho$ represents the density of the fluid sample;
$\rho_{wbm}$ represents the water based mud filtrate density.

6. The method according to claim 1, wherein the determining the existence of the high quality pressure gradient at the downhole conditions is performed through a downhole pretest.

7. A method for contamination monitoring, comprising:
measuring via a downhole apparatus water based mud filtrate density and resistivity at downhole conditions;
logging via the downhole apparatus properties of a downhole fluid to find at least a resistivity and a density of a fluid sample at the downhole conditions;
establishing via the downhole apparatus a linear relationship between a water based mud filtrate conductivity at downhole conditions and the water based mud filtrate density at the downhole conditions;
determining via the downhole apparatus an existence of a high quality pressure gradient at the downhole conditions;
fitting via the downhole apparatus at least one of a density and a resistivity data for native formation water using a power function and obtaining at least one of a density and a resistivity for native formation water when no high quality pressure gradient exists;
estimating via the downhole apparatus the density for native formation water from the pressure from the high quality gradient when the high quality pressure gradient exists;
estimating via the downhole apparatus the resistivity for native formation water, using the linear relationship between the water based mud filtrate conductivity and the water based mud filtrate density;
estimating via the downhole apparatus a density for water based mud filtrate using the linear relationship between the water based mud filtrate conductivity and the water based mud filtrate density; and
estimating via the downhole apparatus a water based mud filtrate contamination based on the water based mud filtrate density.

8. The method according to claim 7, wherein the estimating the resistivity for native formation water is performed using the linear relationship between the water based mud filtrate conductivity and the water based mud filtrate density.

9. The method according to claim 7, wherein the estimating the resistivity for native formation water is performed using Archie's expression $$R_{wf} = \frac{1}{a}\varphi^m S_w^n R_t \approx \frac{1}{.8}1\varphi^2 R_t$$

where $R_{wf}$ represents resistivity of native formation water;
a represents a constant;
$\varphi$ represents a formation porosity;
m represents a cementation factor;
$S_w$ represents water saturation;
n represents a saturation exponent;
$R_t$ represents a formation resistivity.

10. The method according to claim 7, further comprising: estimating a time required for sampling to reach a water based mud filtrate contamination level.

11. The method according to claim 7, wherein the estimating the water based mud filtrate contamination is performed through an equation:

$$\eta = \frac{\frac{1}{R^n} - \frac{1}{R_{fw}^n}}{\frac{1}{R_{wbm}^n} - \frac{1}{R_{fw}^n}} = \frac{\rho_{fw} - \rho}{\rho_{fw} - \rho_{wbm}}$$

where $\eta$ represents the water based mud filtrate contamination;
R represents the resistivity of the fluid sample;
$R_{fw}$ represents the resistivity of native formation water;
$R_{wbm}$ represents the water based mud filtrate resistivity;
n represents an adjustable parameter;
$\rho_{fw}$ represents the density of native formation water;
$\rho$ represents the density of the fluid sample;
$\rho_{wbm}$ represents the water based mud filtrate density.

12. The method according to claim 7, wherein the determining the existence of the high quality pressure gradient at the downhole conditions is performed through a downhole pretest.

* * * * *